(12) United States Patent
Pyatnitsky et al.

(10) Patent No.: US 11,867,662 B2
(45) Date of Patent: Jan. 9, 2024

(54) APPARATUS FOR MULTISENSOR ELECTROMAGNETIC DEFECTOSCOPY AND INTEGRITY MONITORING OF WELL CASINGS

(71) Applicant: LIMITED LIABILITY COMPANY "MIKS", Moscow (RU)

(72) Inventors: Dmitry Yurievich Pyatnitsky, Saratov (RU); Andrey Alexandrovich Arbuzov, Kazan (RU); Dmitry Alexandrovich Davydov, Kazan (RU); Alexey Yurievich Vdovin, Astrakhan (RU)

(73) Assignee: TGT DMCC, Dubai (AE)

( * ) Notice: Subject to any disclaimer, the term of this patent is extended or adjusted under 35 U.S.C. 154(b) by 301 days.

(21) Appl. No.: 17/297,698

(22) PCT Filed: Jul. 1, 2019

(86) PCT No.: PCT/RU2019/050099
§ 371 (c)(1),
(2) Date: May 27, 2021

(87) PCT Pub. No.: WO2020/111979
PCT Pub. Date: Jun. 4, 2020

(65) Prior Publication Data
US 2022/0026392 A1     Jan. 27, 2022

(30) Foreign Application Priority Data
Nov. 28, 2018   (EA) .................................. 201800606

(51) Int. Cl.
*G01N 27/90*     (2021.01)
*G01N 33/2045*   (2019.01)
*E21B 47/00*     (2012.01)

(52) U.S. Cl.
CPC ....... *G01N 27/9006* (2013.01); *E21B 47/006* (2020.05); *G01N 33/2045* (2019.01)

(58) Field of Classification Search
CPC ........ G01N 27/72; G01N 27/80; G01N 27/82; G01N 27/87; G01N 27/90; G01N 27/9006;
(Continued)

(56) References Cited

U.S. PATENT DOCUMENTS 5,144,565 A * 9/1992 Brown ............... G01N 27/9046
702/38
5,293,117 A * 3/1994 Hwang .................. G01N 27/82
324/242

(Continued)

FOREIGN PATENT DOCUMENTS

CN      102691496 A  *  9/2012  ............. E21B 47/00
DE   102014114226 A1  *  3/2016  ............. G01N 27/80
(Continued)

OTHER PUBLICATIONS

Zhao et al.; Translation of CN-102691496-A; Published by EPO & Google (Year: 2012).*
(Continued)

*Primary Examiner* — Steven L Yeninas
*Assistant Examiner* — Rahul Maini
(74) *Attorney, Agent, or Firm* — Sughrue Mion, PLLC

(57) ABSTRACT

The apparatus is useful for monitoring integrity of casings, tubings, and other tubular strings in oil and gas wells. An apparatus for defectoscopy of downhole casings includes several units in a housing. An electromagnetic field generation unit generates excitation pulse of a specified amplitude and duration. It includes an exciter coil containing a core made a high magnetic permeability material. A pick-up sensor unit includes an integral pick-up coil and radial
(Continued)

pick-up coils mounted around the exciter coil winding. Each pick-up coil has a U-shaped core with poles directed perpendicularly to the surveyed pipe surface and having a center line parallel to the center line of the exciter coil winding. A data control, acquisition, and processing unit includes operational amplifiers with variable amplification factors and analog-to-digital converters (ADCs) that transmit signals from the pick-up coils to software for casing defect analysis.

9 Claims, 3 Drawing Sheets

(58) Field of Classification Search
CPC ............ G01N 27/9013; G01N 27/902; G01N 27/904; G01N 27/9046; G01N 27/9053; G01N 27/9073; G01N 27/908; G01N 27/9093; G01N 33/2045; E21B 47/006; E21B 47/007
USPC ................. 324/228, 229, 232, 234, 236–243
See application file for complete search history.

(56) References Cited

U.S. PATENT DOCUMENTS

| | | | | |
|---|---|---|---|---|
| 5,532,587 | A * | 7/1996 | Downs | G01N 27/902 324/242 |
| 7,403,000 | B2 * | 7/2008 | Barolak | E21B 47/085 324/345 |
| 9,772,308 | B2 * | 9/2017 | Davydov | G01N 27/90 |
| 10,539,701 | B2 * | 1/2020 | Kawano | G01R 33/02 |
| 2009/0195244 | A1 | 8/2009 | Mouget et al. | |
| 2016/0061776 | A1 | 3/2016 | Aslanyan et al. | |
| 2018/0196005 | A1 * | 7/2018 | Fanini | G01N 27/83 |

FOREIGN PATENT DOCUMENTS

| | | | |
|---|---|---|---|
| RU | 2 215 143 | 10/2003 | |
| RU | 2 372 478 | 11/2009 | |
| RU | 2 468 197 | 11/2012 | |
| RU | 138 022 | 2/2014 | |
| RU | 2635120 C1 * | 11/2017 | ............ C25D 11/02 |

OTHER PUBLICATIONS

Yurevich et al.; Translation of RU-2635120-C1; Published by EPO & Google (Year: 2017).*

Gopalan et al.; Translation of DE-102014114226-A1; Published by EPO & Google (Year: 2016).*

International Search Report for PCT/RU2019/050099, dated Oct. 17, 2019, 2 pages.

Written Opinion of the ISA for PCT/RU2019/050099, dated Oct. 17, 2019, 4 pages.

* cited by examiner

APPARATUS FOR MULTISENSOR ELECTROMAGNETIC DEFECTOSCOPY AND INTEGRITY MONITORING OF WELL CASINGS

This application is the U.S. national phase of International Application No. PCT/RU2019/050099 filed 1 Jul. 2019, which designated the U.S. and claims priority to EA Patent Application No. 201800606 filed 28 Nov. 2018, the entire contents of each of which are hereby incorporated by reference.

TECHNICAL FIELD

The invention relates to geophysical surveys and can be utilised for monitoring integrity of casings, tubings and other tubular strings in oil and gas wells.

BACKGROUND ART

There is a known electromagnetic module, MTT of Sondex, to identify defects in tubing strings (Magnetic thickness tools-MTT. Leading Oilfield Technology. Sondex, p. 10, http://www.sondex.com). The MTT consists of one exciter coil and 12 miniature magnetic sensors mounted on the inside of bow springs. The generator operates at three frequencies. The signal amplitude and phase at the pick-up coil depend on the amount of metal surrounding a sensor. The drawback of this known logging tool is that, while it can identify defects in one tubing string or an interval of the casing string after withdrawal from tubing, it cannot distinguish between defects on the inner and outer sides of a string.

There is a known RF patent No. 2215143, The Downhole Electromagnetic Defectoscope, published 27 Oct. 2003, which discloses a device that can identify defects and perforations in pipe strings. The downhole electromagnetic defectoscope comprises a housing, an exciter coil with its magnetic axis being aligned with the defectoscope axis, and a pick-up coil with its magnetic axis being perpendicular to the defectoscope axis. An alternating current is fed into the exciter coil to generate loop eddy currents in the surrounding steel pipe, and those, in turn, induce an EMF in pick-up coils. As the pick-up coils pass by defects in the casing string, characteristic changes in the magnetic field are observed.

The closest to the proposed solution is a defectoscope disclosed in RF Patent No. 2372478, The Downhole Electromagnetic Defectoscope, published 10 Nov. 2009. The patent describes a device that uses several (more than three) inductive pick-up coils located peripherally around the device, with their magnetic axes being perpendicular to the device axis. The device operates on a logging cable and contains a longitudinal inductive exciter coil coaxial with the device and at least three pick-up coils located peripherally around the device, with their magnetic axes being perpendicular to the exciter coil axis. The defectoscope operates in the following manner: a single-pole magnetising pulse current of constant amplitude and frequency and uniform duration is fed into the exciter coil to generate eddy currents in the surrounding steel pipe. The pick-up coils register the EMF of transient processes as a function of time. The measurement module operated by a controller separates in time the signals from inductive pick-up coils, amplifies and digitises them, and then transmits the data to surface via communication lines. The drawback of the known device is that it is impossible to dispose of mutual interference of the inductive pick-up coils located circumferentially around the device, especially if it is of a small diameter (less than 50 mm). Also, the inductive pick-up coils that are perpendicular to the surveyed surface have only one active pole, while the second pole is away from the surveyed surface by the coil length, which reduces the coil sensitivity to magnetic field variations on the surveyed surface. With such inductive pick-up coil design, a defect can be detected in a wider radial sector. More specifically, the known device can detect a local pinhole defect in 180° sector. Also, as the pick-up coils of the known device are arranged perpendicularly to the exciter coil magnetic axis, they are sensitive only to deviations of a uniform magnetic field of eddy currents excited by the exciter coil field variations, because the eddy-current field in the absence of any defects and electromagnetic anomalies at the pick-up coils is parallel to the exciter coil magnetic axis. Consequently, the pick-up coils of the known device are incapable of tracking thickness variations on long spans of the surveyed pipe, i.e. in extensive corrosion zones. Also, the fact that the signal on the coils does not depend on the surveyed pipe thickness makes it impossible to estimate the thickness numerically.

DISCLOSURE OF INVENTION

The object of the invention is to create an instrument for magnetic-induction defectoscopy of pipe in downhole strings, which will enhance the informative value of measurements in surveyed pipes both longitudinally and azimuthally.

The technical result consists in an improved accuracy of the defectoscopy.

To meet the specified objective, an apparatus for downhole casing defectoscopy is proposed, which comprises an electromagnetic field generation unit, pick-up sensor unit, and data acquisition and processing unit, with all these units mounted in a housing, and, specifically:

electromagnetic field generation unit for generation of excitation pulse of specified amplitude and duration is essentially an exciter coil containing a core made of a material with a high magnetic permeability;

Pick-up sensor unit comprises an integral pick-up coil and a plurality of radial pick-up coils mounted around the exciter coil winding, each pick-up coil having a U-shaped core with poles directed perpendicularly to the surveyed pipe surface and centre line of the winding is parallel to the centre line of the exciter coil winding;

Data control, acquisition and processing unit comprises a plurality of operational amplifiers with variable amplification factors and analogue-to-digital converters (ADC) that transmit signals from pick-up coils to microcontroller connected to a PC with software for casing defect analysis installed. The microcontroller controls the electromagnetic field generation unit, as well as amplification factors and ADC;

In one embodiment of the invention the apparatus may be designed so that the radial pick-up coils are positioned radially symmetrically in respect to the exciter coil winding centre line.

In another embodiment of the invention the apparatus may be designed so that the integral pick-up coil may be wound on the same core as the exciter coil;

In another embodiment of the invention the apparatus may be designed so that the electronic part contains a power supply unit which comprises stabilizers and ensures uninterruptable operation of the electronics.

In another embodiment of the invention the apparatus may be designed so that the data control, acquisition and processing unit comprises an excitation pulse generator which is essentially a current-controlled voltage inverter to generate bipolar excitation of magnetic field by the exciter coil, which makes it possible to eliminate the effect produced by local magnetised areas of the surveyed pipe.

In another embodiment of the invention the apparatus may be designed so that in order to improve its sensitivity an electronic circuit is used to provide the switchable amplification factor, which makes it possible to record one and the same response in two stages, with the response being recorded at the second stage at a higher amplification factor.

The description contains an embodiment wherein the apparatus comprises 8 radial pick-up coils. This notwithstanding, the claimed technical result can be achieved by using an alternative quantity of radial coils.

The apparatus body may be made of a conducting nonmagnetic metal.

The apparatus may additionally comprise a turn indicator to account for axial rotation of the apparatus as it is conveyed along the wellbore.

EMBODIMENT OF THE INVENTION

Defectoscopy accuracy is enhanced by applying in the proposed apparatus design of at least three identical, radially symmetrically positioned, bipolar U-shaped pick-up sensors with their cores being coaxially arranged with the exciter coil winding, and the U-shaped cores that are made of a material with a high magnetic permeability form sensor poles that are positioned at maximum proximity to the surveyed surface, with the sensors being equidistant from the surveyed surface. Thereby, the maximum focusing effect of the sensors in respect to the surveyed surface is achieved.

To enhance azimuthal resolution, the number of sensors may be increased within the restrictions imposed on the maximum diameter of the logging tool. In order to ensure that sensitivity ranges are overlapping radially, the maximum chordwise distance between two adjacent sensors should be less than or equal to the sensor length.

Application of exciter coil and pick-up coils sensors made of a material with a high magnetic permeability increases the energy of generated field and sensitivity of sensors, which makes it possible to use some conducting nonmagnetic metals in the tool housing instead of costly radiotransparent materials.

The proposed tool is additionally equipped with an integral pick-up coil that is wound on the same core as the exciter coil. This permits estimation of the surveyed casing string total thickness as an additional parameter, determination of the second casing string design and, primarily, the locations of casing collars, thereby improving interpretation accuracy by accounting for the effect produced by the second casing string on the registered signal.

In the proposed invention the pick-up sensor winding is positioned coaxially with the exciter coil winding, which makes the sensors sensitive not only to defects and electromagnetic anomalies of the surveyed pipe but also to its width, thus permitting metal loss estimation in the sensitive area of the sensor.

Figure 1:
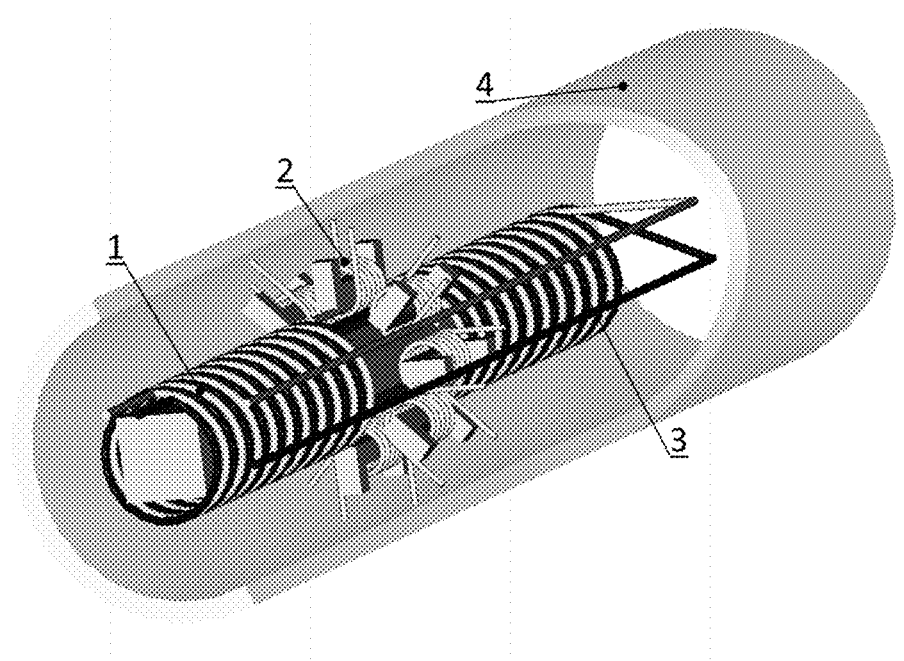
FIG. 1-3 show a three-dimensional model and cross-sections of the sensor component of the apparatus. The items are referenced as follows:
Item 1—Exciter coil on a core with a high $\mu$,
Item 2—Radial pick-up coils on U-shaped cores,
Item 3—Integral pick-up coil on a core with a high $\mu$,
Item 4—Protective housing made of a nonmagnetic alloy.
Figure 2:
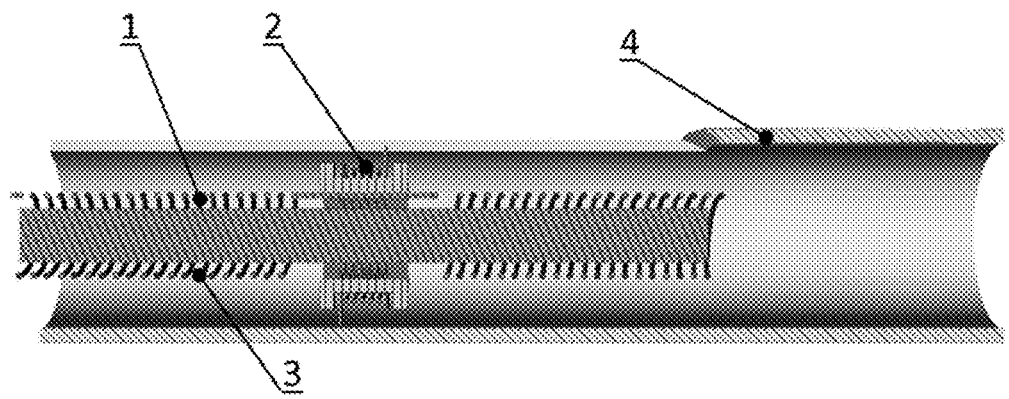
Figure 3:
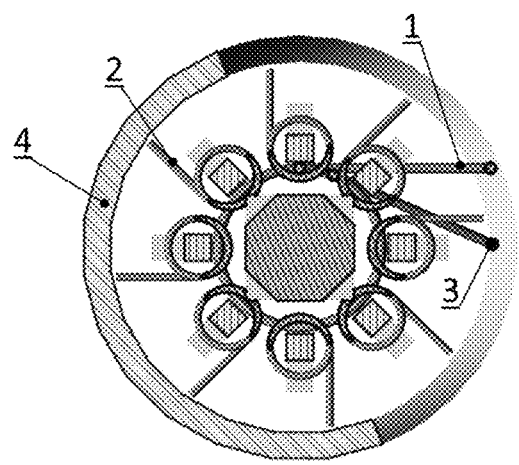
Figure 4:
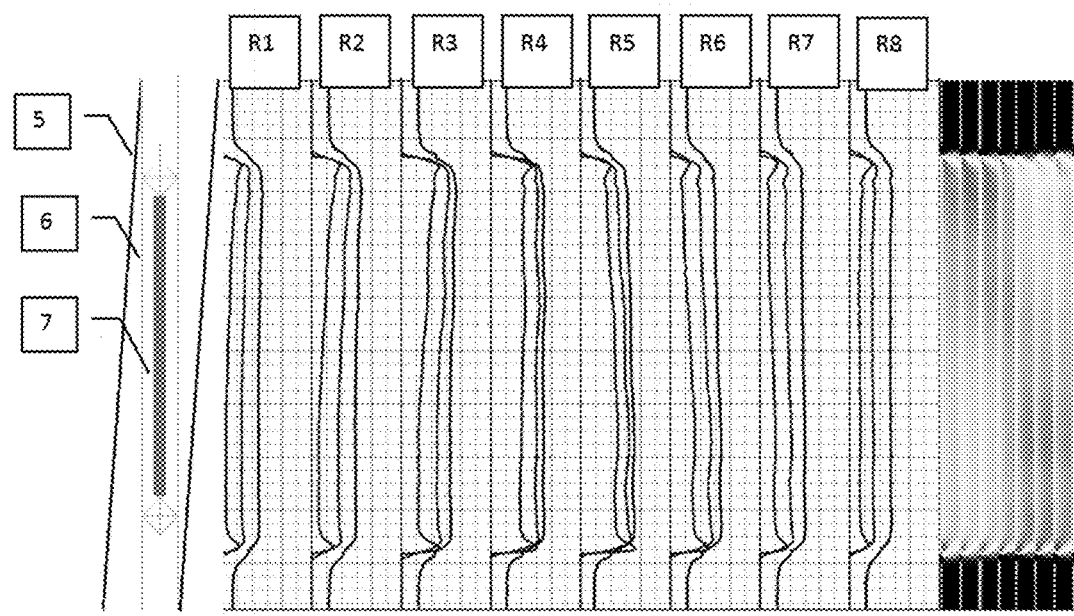
FIG. 4 shows an off-centred tubing string inside a casing and corresponding readings on the radial pick-up coils. The items are referenced as follows:
Item 5—Casing,
Item 6—Tubing,
Item 7—Logging tool.
Figure 5:
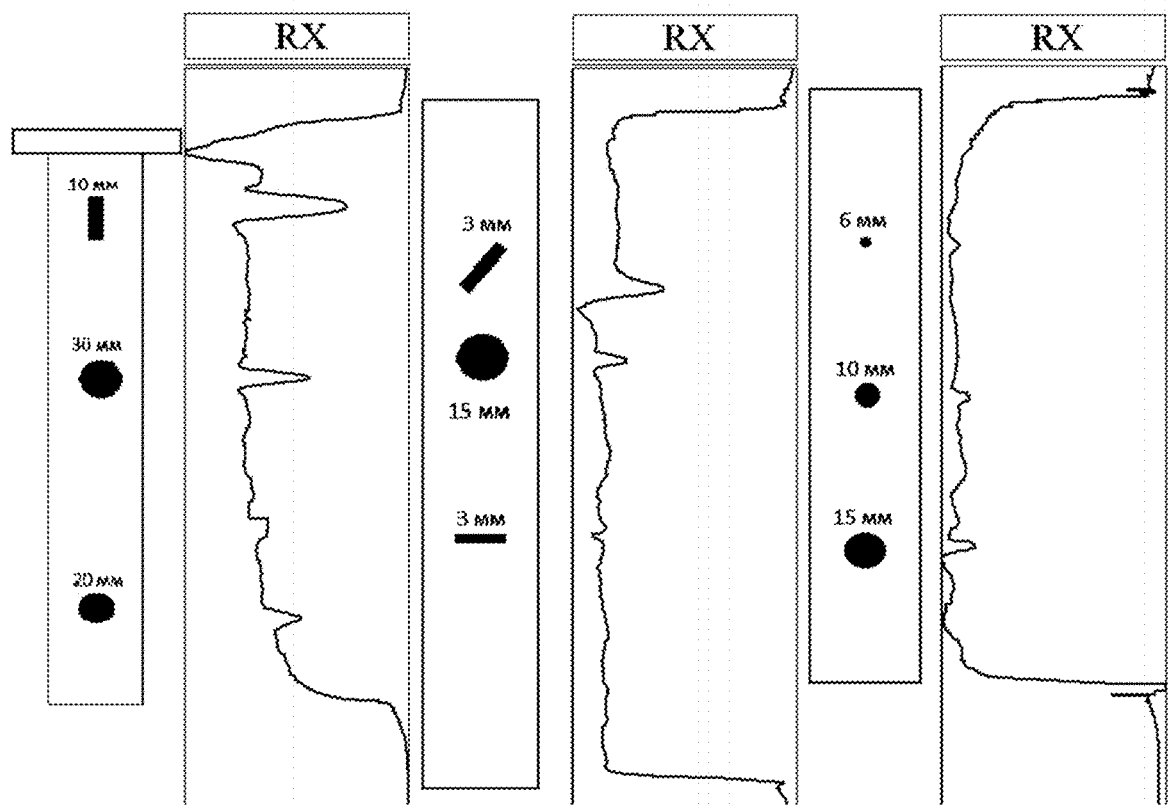
FIG. 5 shows some cases of local defect detection on various tubulars.

Signal level at the sensor will also be affected by the presence of casing strings and surface pipes positioned externally in respect to the surveyed pipe. Thus is due to the fact that if the exciter coil is of sufficient length and power, eddy currents will be generated also in the pipes positioned externally in respect to the surveyed pipe. Research has experimentally proven that eddy currents in external pipes will be effectively generated at coil lengths being 4/3 of the surveyed pipe diameter. Accordingly, if the sensors are positioned radially symmetrically, as proposed, and the tool is centred inside the surveyed pipe, the level of signals at different sensors will depend on the surveyed pipe position in respect to outer casing or surface pipe, which provides an opportunity to implement the method of estimating how far off-centre the surveyed pipe is inside the casing string. If the well completion is properly centred, the distance between surveyed pipe and external casing will be radially equal and, accordingly, pick-up sensor signals will be on the same level. If the surveyed pipe is off-centre inside the casing, the signal levels will differ, with the signal level of any specific pick-up sensor being so much higher as the surveyed pipe within the sensor range is closer to the outer casing, and vice versa (FIG. 5). FIG. 5 shows a log recorded by logging tool (7), with tubing (6) intentionally off-centred inside casing (5). The signals registered by radial pick-up coils R4 and R8 do not change as the tool moves forward along the pipe and the signals registered by radial pick-up coils R2 and R6 have the highest mutually antithetical decline. Thuswise, radial pick-up coil R2 is at maximum proximity to the casing in the upper part of the model and, conversely, radial pick-up coil R6 is at maximum proximity to the casing in the lower part of the model and the tool can determine the degree of tubing decentring inside the casing.

To estimate decentring and take into account tool's axial rotation in time as it moves along the tubing string, it is essential to know the mutual alignment of pipe and pick-up sensors. This information can be obtained by using a device for measuring the tool's angle of rotation in time (for example, a conventional inclinometer or a gyroscope). As long as this information is available, the sensor position can be adjusted. The angle measuring device may be designed either as a separate module being a part of the logging tool or as a standalone instrument.

Besides this, the defectoscopy accuracy can be enhanced by applying a method of bipolar excitation of magnetic field with an exciter coil, alternating exciter pulses of different polarity, which allows elimination of the effects produced by locally magnetised areas of the surveyed pipe.

Figure 6:
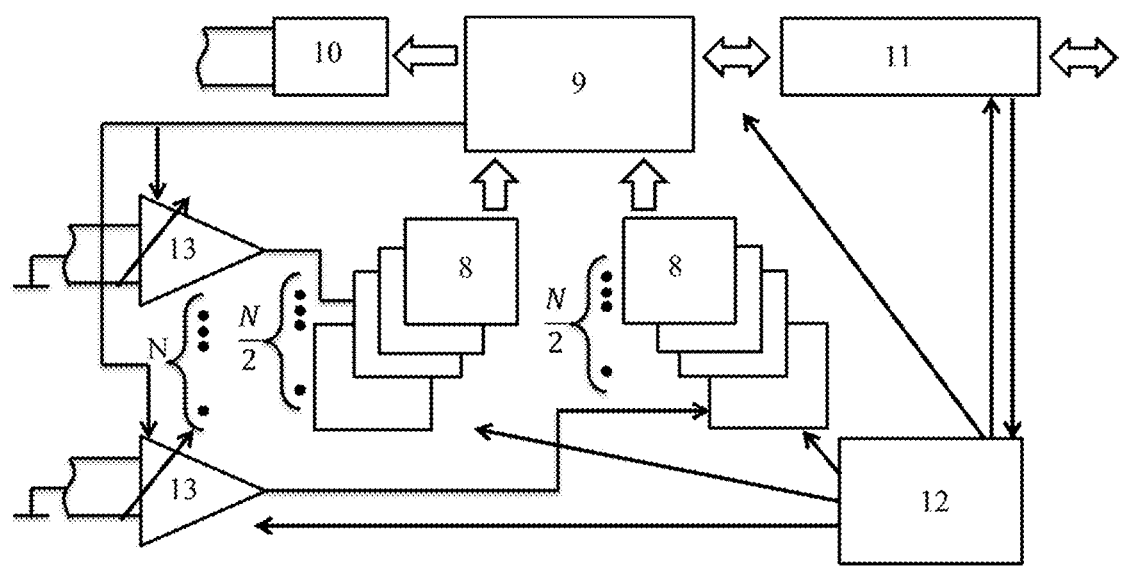
FIG. 6 shows a block diagram of the apparatus electronics. The items are referenced as follows:
Item 8—Analogue-to-digital converters (ADC),
Item 9—Microcontroller module with ROM,
Item 10—Excitation pulse generator,
Item 11—Interface module,
Item 12—Power supply unit,
Item 13—Operational amplifiers.

The block diagram of tool electronics (FIG. 6) reflects the following major functions: excitation pulse generation, data acquisition and recording, data analysis and data storage in tool memory. The generation module (10) generates excitation pulses of a specified frequency and changes pulse polarities, thus enabling the usage of bipolar mode of operation. This module is controlled by a microcontroller (9) and is physically positioned in close proximity to the latter. The data are acquired and recorded by operational amplifiers (13) with a variable amplification factor controlled by microcontroller (9) and ADC (8). Physically, there could be a plurality of operational amplifiers (13), this being determined by the number of pick-up coils. The ADC (8) records one and the same response in two stages: first at earlier times and with a lower amplification factor, and then at later times and with a higher amplification factor, this enhancing the tool sensitivity. The pick-up coil has a feature where virtual ground with the potential equal to half of the level than can be processed by ADC (8) is used instead of regular ground This feature helps to dispose of an additional negative supply shaping circuit, thus reducing noises, which is taken into account as the data are processed. In the process of data analysis the data received from the ADC are allocated in the tool memory, forming data frames which afterwards are read out by data processing software. The tool communicates with the PC via an interface module (11). The tool power supply unit (12) comprises several stabilisers that maintain the required supply voltage levels in tool electronics.

The microcontroller embedded software supports two modes of tool operation: memory mode and real-time logging mode. In memory mode the tool is programmed from a PC and the required logging programme (cyclogram) is launched at surface, and then a logging survey is carried out with power being supplied to the tool from a standalone battery pack. Once the logging operation is over the tool is reconnected to the PC to upload the data for an analysis. In real-time logging mode, programming and data acquisition is performed interactively, with the tool being in constant communication with the PC. Power is supplied and data are transmitted via a logging cable.

The invention claimed is:

1. An apparatus for defectoscopy of downhole casings, comprising:
    an electromagnetic field generator configured to generate an excitation pulse of a specified amplitude and duration, electromagnetic field generator being an exciter coil containing a core made of a high magnetic permeability material:
    a pick-up sensor comprising an integral pick-up coil and a plurality of radial pick-up coils, wherein the plurality of radial pick-up coils are mounted between opposing end portions of the exciter coil and around the core, each of the radial pick-up coils having a U-shaped core with poles directed perpendicularly away form the core, wherein center lines of the integral pick-up coil and the plurality of radial pick-up coils are aligned with a center line of the exciter coil, wherein turns of the integral pick-up coil and the exciter coil alternate along a longitudinal axis of the core such that at least one section of the integral pick-up coil is located between two sections of the exciter coil and vice versa;
    a controller comprising a plurality of operational amplifiers with variable amplification factors and analog-to-digital converters (ADCs), wherein the controller is configured to transmit signals from the radial pick-up coils to a computer with casing defect analysis software installed thereon, the computer being configured to control the electromagnetic field generator, the amplification factors, and the ADCs,
    wherein the electromagnetic field generator, the pick-up sensor, and the controller are all mounted in a housing.

2. The apparatus according to claim 1, wherein the radial pick-up coils are positioned radially symmetrically in respect to the center line of the exciter coil.

3. The apparatus according to claim 2, wherein the integral pick-up coil is wound on the same core as the exciter coil.

4. The apparatus according to claim 3, further comprising a power supply that comprises power supply stabilizers to promote uninterrupted operation of the apparatus.

5. The apparatus according to claim 4, wherein a current-controlled voltage inverter is configured to generate bipolar excitation of a magnetic field by the exciter coil in a manner sufficient to compensate for an effect produced by local magnetized areas of a surveyed pipe.

6. The apparatus according to claim 5, wherein a given amplification factor is provided so that one response is recordable in first and second stages, with the response being recorded at the second stage being at a higher amplification factor than the first stage.

7. The apparatus according to claim 1, wherein the apparatus has eight radial pick-up coils.

8. The apparatus according to claim 1, wherein the housing is made of a conducting nonmagnetic metal.

9. The apparatus according to claim 1, further comprising a turn indicator configured to account for axial rotation as the apparatus is conveyed along a wellbore.

* * * * *